(12) United States Patent
Mirov et al.

(10) Patent No.: US 9,451,911 B1
(45) Date of Patent: Sep. 27, 2016

(54) TEST MODEL FOR WEARABLE DEVICES

(71) Applicant: Verily Life Sciences LLC, Mountain View, CA (US)

(72) Inventors: Russell Norman Mirov, Mountain View, CA (US); John Lapetina, Mountain View, CA (US); Mark Askew, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 70 days.

(21) Appl. No.: 14/308,278

(22) Filed: Jun. 18, 2014

(51) Int. Cl.
*G01N 21/55* (2014.01)
*A61B 5/1495* (2006.01)
*G01N 21/47* (2006.01)

(52) U.S. Cl.
CPC ......... *A61B 5/1495* (2013.01); *G01N 21/4738* (2013.01); *G01N 2201/061* (2013.01)

(58) Field of Classification Search
CPC combination set(s) only.
See application file for complete search history.

(56) References Cited

U.S. PATENT DOCUMENTS

| | | | |
|---|---|---|---|
| 4,834,532 A | 5/1989 | Yount | |
| 5,891,025 A | 4/1999 | Buschmann et al. | |
| 7,214,190 B1 | 5/2007 | Wilson | |
| 7,346,378 B2 | 3/2008 | Ruiter | |
| 7,701,580 B2 | 4/2010 | Bassler et al. | |
| 7,763,856 B2 | 7/2010 | Kiesel et al. | |
| 7,797,035 B2 | 9/2010 | Ostrovsky | |
| 7,817,254 B2 | 10/2010 | Hegyi et al. | |
| 7,817,276 B2 | 10/2010 | Kiesel et al. | |
| 7,844,314 B2 | 11/2010 | Al-Ali | |
| 7,894,068 B2 | 2/2011 | Bassler et al. | |
| 8,153,949 B2 | 4/2012 | Kiesel et al. | |
| 8,323,188 B2 | 12/2012 | Tran | |
| 8,344,731 B2 | 1/2013 | Lee | |
| 8,368,402 B2 | 2/2013 | Lee et al. | |
| 2004/0259270 A1 | 12/2004 | Wolf | |
| 2005/0054907 A1 | 3/2005 | Page et al. | |
| 2007/0255122 A1 | 11/2007 | Vol et al. | |
| 2010/0049010 A1 | 2/2010 | Goldreich | |
| 2011/0028803 A1 | 2/2011 | Ollmar | |
| 2011/0117028 A1 | 5/2011 | Zharov | |

OTHER PUBLICATIONS

Stuban, Norbert, et al. "Phantom with Pulsatile Arteries to Investigate the Influence of Blood Vessel Depth on Pulse Oximeter Signal Strength", Sensors 2013, 12 (1), 895-904, Jan. 16, 2012. ISSN 1424-8220. www.mdi.com/journal/sensors.

(Continued)

*Primary Examiner* — Tri T Ton
(74) *Attorney, Agent, or Firm* — McDonnell Boehnen Hulbert & Berghoff LLP (57) ABSTRACT

A test model for simulating one or more physiological parameters is provided. In one example, the test model includes a model layer having a test surface, a shaft rotatably disposed within the model layer and at least first and second contrast segments circumferentially disposed on the shaft. The model layer models at least one optical property of human skin, such as transmissivity of at least a particular wavelength of light transmitted into the model layer. The first and second contrast segments have contrasting optical properties with regard to at least the particular wavelength of light, such as reflectance. Rotation of the shaft causes different contrast segments to face the test surface of the model layer at different times.

20 Claims, 8 Drawing Sheets

(56) References Cited

OTHER PUBLICATIONS

Manuel Arruebo, Mónica Valladares, and África González-Fernández, Antibody-Conjugated Nanoparticles for Biomedical Applications, Journal of Nanomaterials, vol. 2009 (2009), Article ID 439389, 24 pages (available at http://dx.doi.org/10.1155/2009/439389).

Shao et al, "Magnetic nanoparticles for biomedical NMR-based diagnostics," Beilstein Journal of Nanotechnology, 2010, 1, 142-154.

Liu et al, "Magnetic resonance monitoring of focused ultrasound/magnetic nanoparticle targeting delivery of therapeutic agents to the brain," PNAS Early Edition, 2010, pp. 1-6.

TEST MODEL FOR WEARABLE DEVICES

BACKGROUND

Unless otherwise indicated herein, the materials described in this section are not prior art to the claims in this application and are not admitted to be prior art by inclusion in this section.

A number of scientific methods have been developed in the medical field to evaluate a person's health state. A person's health state may, for example, be evaluated based on the measurement of one or more physiological parameters, such as blood pressure, pulse rate, skin temperature, or galvanic skin response (GSR). In a typical scenario, these measurements may be taken in the home or a health-care setting by using several discreet devices or sensors and, in some cases, by drawing blood or other bodily fluid. For most people, the measurements or blood tests are performed infrequently, and changes in a physiological parameter, which may be relevant to health state, may not be identified, if at all, until the next measurement is performed.

In another example, these parameters may be more frequently or continuously measured, and other health-related information obtained, by a wearable device. The device, which may be provided as a wrist-mounted device, may include one or more sensors for detecting or measuring one or more physiological parameters. For example, a wrist-mounted device may include optical sensors for heart rate and blood oxygen saturation ($SpO_2$) monitoring, a thermistor for measuring skin temperature, and a GSR sensor for measuring skin resistance. At least some of the physiological parameter information may be obtained by detecting the presence, absence and/or concentration of one or more analytes in the body.

Calibration and testing of such wearable devices can be important to ensure that the sensors on the device function properly and accurately. In some cases, calibration and testing may be performed by mounting the device on the wrist (or other body surface) of a human subject. However, using a living subject, it is difficult to control or create all of the necessary conditions or ranges to properly test the device. Further, repeatability of testing conditions may also be very difficult to achieve using a living subject. In another example, a simulator device may be used to calibrate and test a wearable device. Currently available simulators are designed to test and calibrate fingertip heart rate and $SpO_2$ measurement devices which operate by measuring the transmission of light through a person's fingertip. These simulators operate by intercepting the light emitted from the emission side of a fingertip monitoring device and replacing it with its own signal, which is received on the detection side of the monitoring device. However, this simulator is not capable of calibrating or testing monitoring devices utilizing reflective sensors. Further, these known simulators are specifically designed to test fingertip monitoring devices and are, therefore, not in the right form for testing a wrist-mounted device.

SUMMARY

Many wearable devices for optically detecting physiological parameters, such as pulse rate and pulse oximetry, detect reflected light originating from a source on the wearable device. This reflected light is modulated by blood flow and interpreted by algorithms to produce information about the physiological parameter. A test-model for testing and calibrating wearable devices of this type may simulate pulsating blood density with a rotating shaft of variable reflectivity inside a model layer (phantom) that mimics one or more optical properties of human skin. Reflected light is modulated by at least two segments on the rotating shaft having different reflectances at a particular wavelength of light. The intensity of the detected signal tracks the rate of rotation of the shaft.

Some embodiments of the present disclosure provide a test model including: a model layer having a test surface, wherein the model layer models at least one optical property of human skin, wherein the at least one optical property modeled by the model layer includes transmissivity of at least a particular wavelength of light transmitted into the model layer through the test surface; a shaft rotatably disposed within the model layer; and at least first and second contrast segments circumferentially disposed on the shaft such that rotation of the shaft causes different contrast segments to face the test surface of the model layer at different times, wherein the first and second contrast segments have contrasting optical properties with regard to at least the particular wavelength of light.

Further embodiments of the present disclosure provide a method including: (1) mounting a wearable device to a test model, wherein the wearable device has at least one light source and at least one detector, wherein the test model comprises: (a) a model layer, wherein the model layer models at least one optical property of human skin, wherein the at least one optical property modeled by the model layer includes transmissivity of at least a particular wavelength of light; (b) a shaft rotatably disposed within the model layer; and (c) at least first and second contrast segments circumferentially disposed on the shaft, wherein the first and second contrast segments have contrasting optical properties with regard to at least the particular wavelength of light; (2) directing light from the light source on the wearable device into the test model while the shaft is rotating, wherein the light from the light source includes light at the particular wavelength; and (3) receiving, by the detector on the wearable device, light reflected from the first and second contrast segments as the shaft is rotating.

Still further embodiments of the present disclosure provide a test model including: (1) a model layer having a test surface, wherein the model layer models at least one optical property of human skin, wherein the at least one optical property modeled by the model layer includes transmissivity of at least a particular wavelength of light transmitted into the model layer through the test surface; (2) a shaft rotatably disposed within the model layer, the shaft having a reflectance with respect to the particular wavelength of light; and (3) a contrast segment provided on the shaft parallel to a longitudinal axis of the shaft such that rotation of the shaft causes the contrast segment to rotate about the longitudinal axis, wherein the contrast segment has a reflectance with respect to the particular wavelength of light, and wherein the reflectance of the shaft is higher than the reflectance of the contrast segment at least with respect to the particular wavelength of light.

These as well as other aspects, advantages, and alternatives, will become apparent to those of ordinary skill in the art by reading the following detailed description, with reference where appropriate to the accompanying drawings.

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

A wearable device can detect one or more physiological parameters, such as heart rate, $SpO_2$, skin temperature and GSR. The device may include one or more light sources for directing light into the body, and one or more detectors for detecting light reflected back from inside of the body. In some examples, the light source may emit light in the red (640 nm), green (540-570 nm) or infrared (840 nm) ranges. In principle, the wearable device may measure pulse rate by sensing an increase in blood density generated by each heartbeat. The reflected light is modulated by blood flow, and may be interpreted by algorithms to produce heart rate, pulse oximetry, and other physiological information. In general, the intensity of light will decrease as the density of blood increases.

The wearable device may also measure blood oxygen level by sensing differences in reflectance due to the amount of oxygen carried by hemoglobin in the blood. In operation, the wearable device directs light of two or more wavelengths into the body. Reflected light is sensed by a detector on the wearable device. The changing reflectance at each of the wavelengths is measured, allowing determination of the reflectances due to the pulsing blood based on the principle that oxygenated and unoxygenated hemoglobin have different levels of reflectively that are wavelength sensitive. The wearable device may further include sensors for detecting skin temperature and resistance.

The term "wearable device," as used in this disclosure, refers to any device that is capable of being worn or mounted at, on, in or in proximity to a body surface, such as a wrist, ankle, waist, chest, ear, eye, head or other body part. As such, the wearable device can collect data while in contact with or proximate to the body. For example, the wearable device can be configured to be part of a contact lens, a wristwatch, a "head-mountable display" (HMD), an orally-mountable device such as a retainer or orthodontic braces, a headband, a pair of eyeglasses, jewelry (e.g., earrings, ring, bracelet), a head cover such as a hat or cap, a belt, an earpiece, other clothing (e.g., a scarf), and/or other devices. Further, the wearable device may be mounted directly to a portion of the body with an adhesive substrate, for example, in the form of a patch, or may be implanted in the body, such as in the skin or another organ.

A testing device may be provided to simulate the pulsating blood density, blood oxygenation, skin temperature and skin resistance of a living subject for testing and calibration purposes. The test model may include a rotating shaft of variable reflectance disposed inside a model layer fabricated from plastic that mimics the light scattering properties of human skin and tissue. In some examples, the plastic may be a plastic resin (epoxy) with various dyes and powders dispersed therein. Optical scatterers may also be used in the plastic to provide different chemical and optical properties. In particular, the optical properties of the plastic may be controlled to mimic the specifics of different groups in the human population (skin tone, age, etc.). The rotating shaft may also be fabricated, in some examples, from a plastic having properties designed to mimic the characteristics of blood. The thickness of the model layer or the position of the shaft within the model layer may be varied to control the intensity and diffusion of the reflected light to mimic different physiological characteristics.

To simulate pulse rate, the light scattering properties of a segment on the circumference of the rotating shaft may be changed to provide contrast with the remainder of the shaft. For example, the shaft may have a color contrasting stripe along its length (or at least within in the field of detection of the wearable device). As the shaft rotates, the contrast stripe will modulate the intensity of the reflected light. The characteristics of the stripe, such as the contrast ratio, shape, symmetry, sharp vs. gradient contrast change, etc., may be adjusted to simulate or test various different conditions. To simulate blood oxygen saturation, a portion of the rotating shaft may be patterned or treated with or fabricated from materials having different reflectance based on the wavelength of incident light. The pulse rate or $SpO_2$ detected by the wearable device will track the rate of rotation of the shaft. The rate of rotation of the shaft can be computer controlled.

The testing device may also be configured to simulate skin temperature and skin resistance to test and calibrate temperature and GSR sensors on a wearable device. In one example, the surface of the model layer may include conductive pads that connect to variable resistances to present the wearable device under test with simulated skin resistances. The wearable device may be mounted on the test model such that the GSR sensor interfaces are positioned over the conductive pads on the surface of the model layer. Further, the surface temperature of the model layer may be controlled to present the device under test with variable skin temperatures. In some examples, temperature control may be achieved by a Peltier device.

It should be understood that the above embodiments, and other embodiments described herein, are provided for explanatory purposes, and are not intended to be limiting.

II. Example Test Models and Wearable Devices

Figure 1:
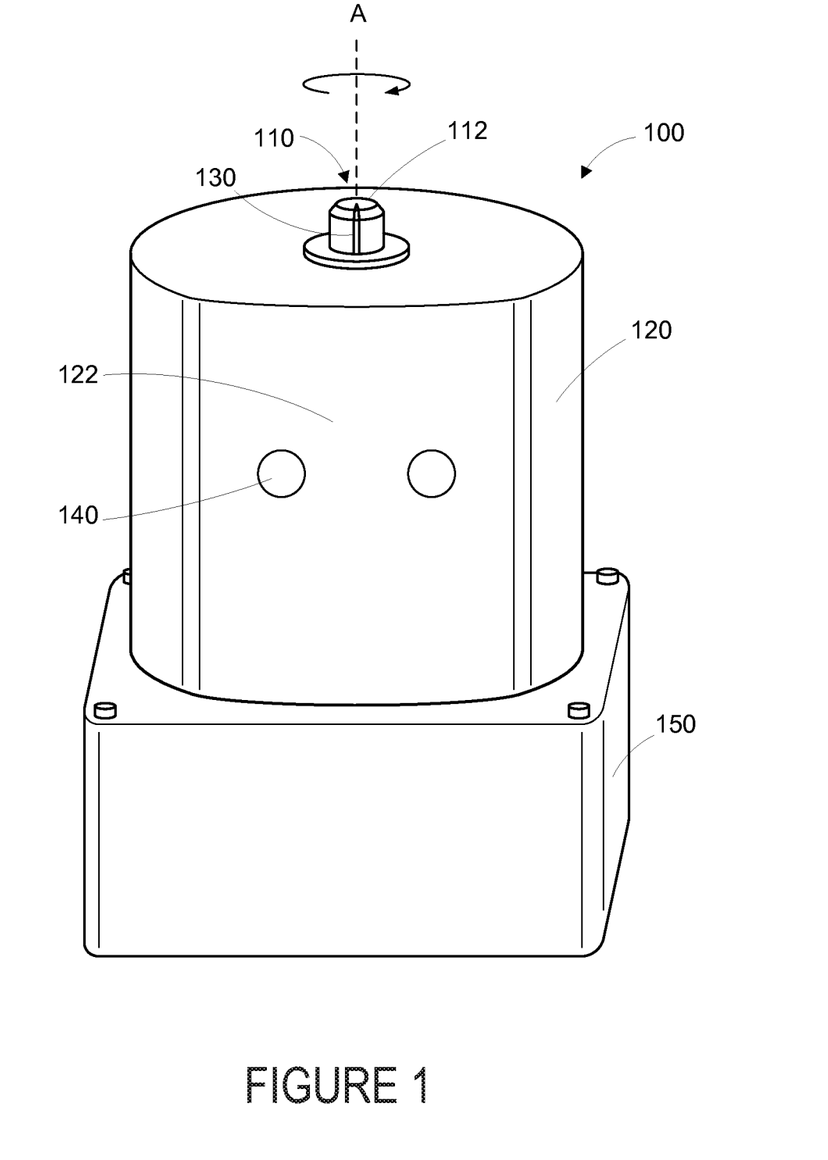
FIG. 1 illustrates an example of a test model.
Figure 2:
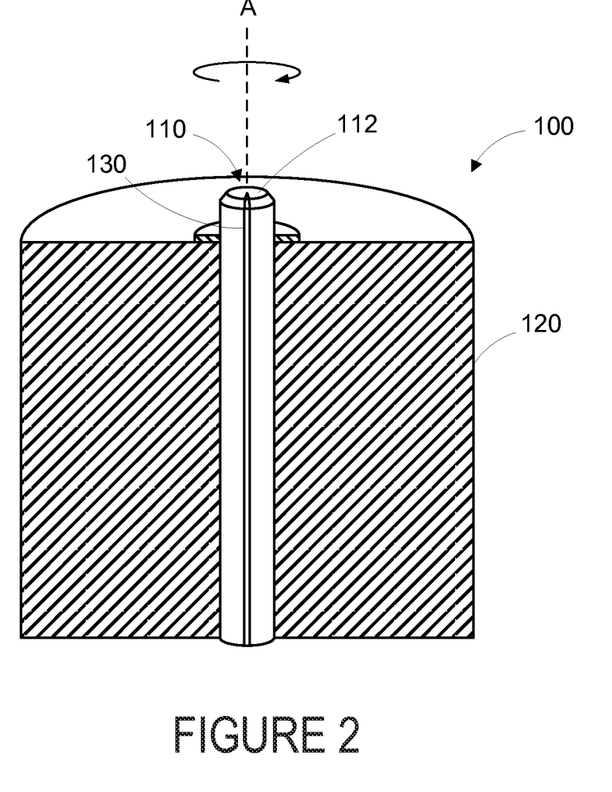
FIG. 2 illustrates a partial cross-sectional view of an example test model.
Figure 3:
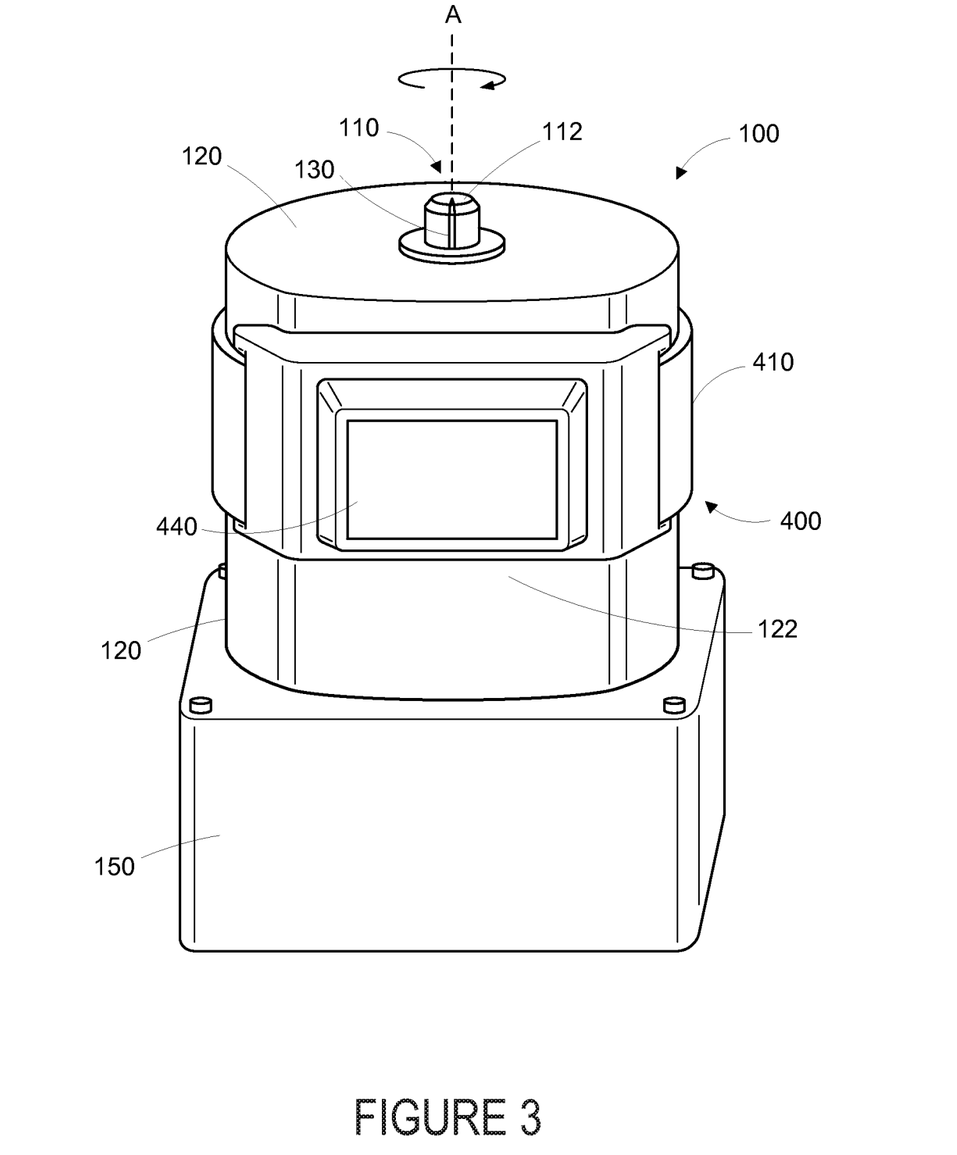
FIG. 3 illustrates an example test model with an example wearable device mounted thereon.

As shown in FIGS. 1 and 2, a test model 100 can be configured to simulate one or more physiological parameters, such as pulsating blood density, blood oxygenation, skin temperature and skin resistance of a living subject, for the purpose of testing and calibrating a wearable device 400. The test model 100 may include an element 110, rotatably disposed within a model layer 120 designed to model at least one optical property of human skin and tissue, such as light transmissivity at a particular wavelength. In on example, as shown in FIGS. 1-3, the element 110 may be provided as a shaft 112. Alternatively, the element 110 may be provided as a rotating disk or looping belt. The element 110 is configured to rotate around an axis A. The axis A may correspond to a longitudinal axis of the shaft 112. The model layer 120 may be fabricated from a plastic, such as a plastic resin or polymer epoxy with various dyes and powders dispersed therein. Optical scatterers may also be used in the model layer 120 to provide different chemical and optical properties. In particular, the optical properties of the model layer 120 may be controlled to mimic the specifics of different groups in the human population (skin tone, age, etc.). The element 110 may also be fabricated, in some examples, from a plastic having properties designed to mimic the characteristics of blood.

A contrast segment 130 may be provided on the circumference of the element 110. The contrast segment 130 may be provided on the element 110 such that it is within the range of detection of one or more sensors on a wearable device 400 mounted over a test surface 122 of the model layer 120 (shown in FIG. 3). In some examples, the contrast segment 130 may run the length of the shaft 112 and may be oriented substantially parallel to the axis A of the shaft 112, as shown in FIG. 2. The contrast segment 130 may have at least one light scattering property in contrast with the remainder of the element 110. For example, contrast segment 130 may be provided as a color contrasting dot or stripe on the element 110, such as a stripe along the length of the shaft 112. The contrast segment 130, in combination with the rest of the element 110, may provide two optically-contrasting segments circumferentially disposed on the element.

The test model 100 may also be configured to simulate skin temperature and skin resistance in order to test and calibrate temperature and GSR sensors on a wearable device 400. One or more conductive pads 140 may be disposed on the test surface 122 of the model layer 120. In order to simulate skin resistance, the conductive pads 140 may be in electrical communication with variable resistances, which may be positioned within or outside of the test model 100, such as in the control unit 150. The wearable device 400 may be mounted on the test model 100 such that the GSR sensor interfaces of the wearable device 400 are positioned over the conductive pads 140 on the test surface 122. Further, the surface temperature of the model layer 120 may be controlled to present the device under test with variable skin temperatures. In some examples, the temperature of the conductive pads 140 may be varied to simulate different skin temperatures. The temperature sensors on the wearable device 400 may be positioned over one or more of the conductive pads 140. Temperature control of the conductive pads 140 may be achieved by a Peltier device.

As shown in FIG. 3, a wearable device 400 may be mounted to an outer surface of the model layer 120, such as, over the test surface 122 of the test model 100. The wearable device 400 may be provided as any device configured to be mounted in, on or adjacent to a body surface. In the example shown in FIGS. 3-5B, the wearable device 400 is a wrist-mountable device, but many other forms are contemplated. In operation, the device may be placed in close proximity to the skin or tissue, but need not be touching or in intimate contact therewith. A mount 410, such as a belt, wristband, ankle band, necklace, or adhesive substrate, etc. can be provided to mount the device 400 at, on or in proximity to the body surface and, during testing or calibration, to the test model 100. In other examples, the wearable device 400 may be provided as or include an eye-mountable device, a head mountable device (HMD) or an orally-mountable device. The test model 100 may be configured to support the testing or calibration of any form of wearable device.

Figure 4A:
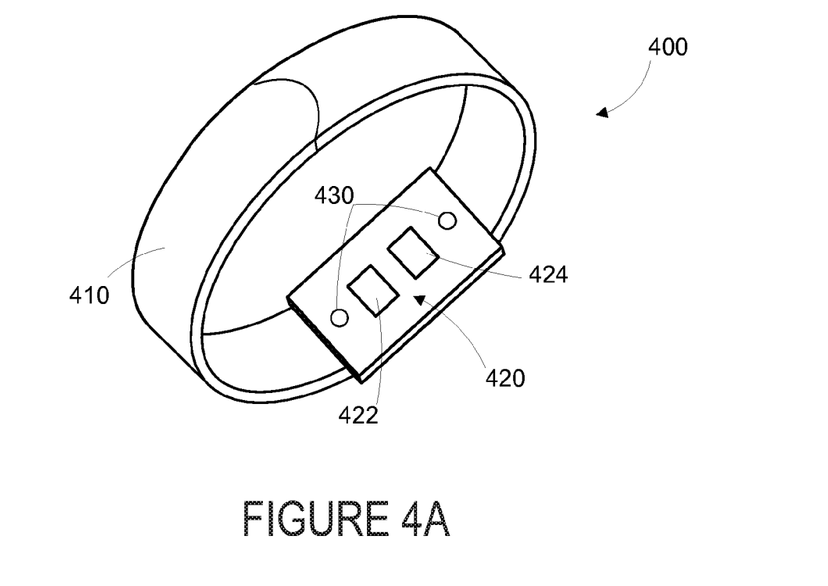
FIG. 4A is a bottom perspective view of an example wearable device.
Figure 4B:
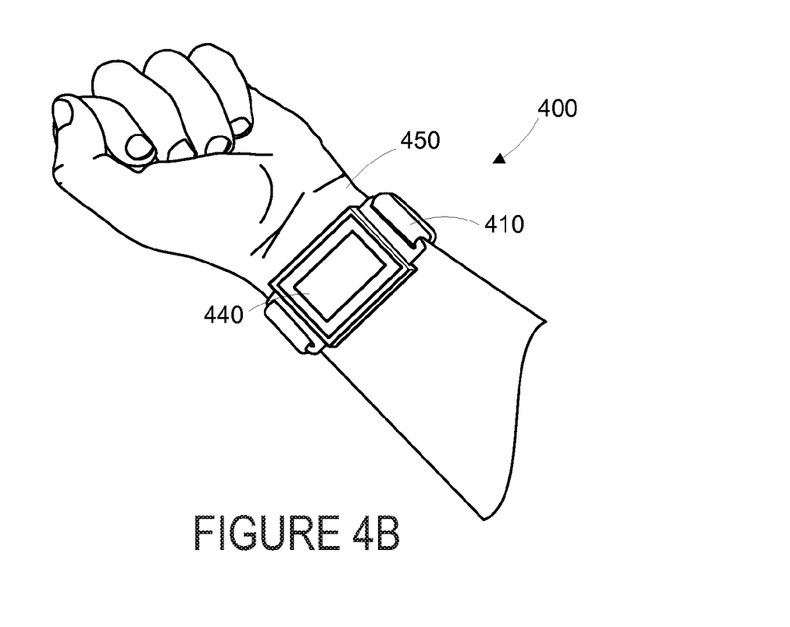
FIG. 4B is an example wearable device, while on a human wrist.

The wearable device 400 may include one or more sensors 420 for sensing one or more physiological parameters of a wearer of the device 400, as shown in FIG. 4A. In some examples, the sensors 420 may be oriented on the wearable device 400 such that they may be positioned on the inner surface of a wearer's wrist 450. The sensors 420 may include any device for collecting, detecting or measuring one or more physiological, motion, contextual or personal parameters. Sensors for detecting and measuring physiological parameters may include, but are not limited to, one or more of an optical (e.g., CMOS, CCD, photodiode), acoustic (e.g., piezoelectric, piezoceramic), electrochemical (voltage, impedance), resistive, thermal, mechanical (e.g., pressure, strain), magnetic, or electromagnetic (e.g., magnetic resonance) sensor. In particular, the wearable device 400 may include a light source 422 and an optical detector 424 and one or more electrodes 430. In some examples, the light source may emit light in the red (640 nm), green (540-570 nm) or infrared (840 nm) ranges. The electrodes 430 may be in electrical communication with a thermometer or a GSR sensor for sensing temperature and skin resistance, respectively. The wearable device 400 may also be equipped to obtain physiological data by non-invasively detecting and/or measuring one or more analytes present in blood, saliva, tear fluid, or other body fluid of the wearer of the device, for example, using an electrochemical or impedimetric sensor. Other types of sensors are contemplated.

The wearable device 400 may also include a display 440 via which the wearer of the device may receive information or notifications, such as recommendations or alerts generated in response to data detected by the device. An indication of the one or more physiological parameters detected or collected by the device 400, such as heart rate, may be provided on the display 440.

Figures 5A, 5C:
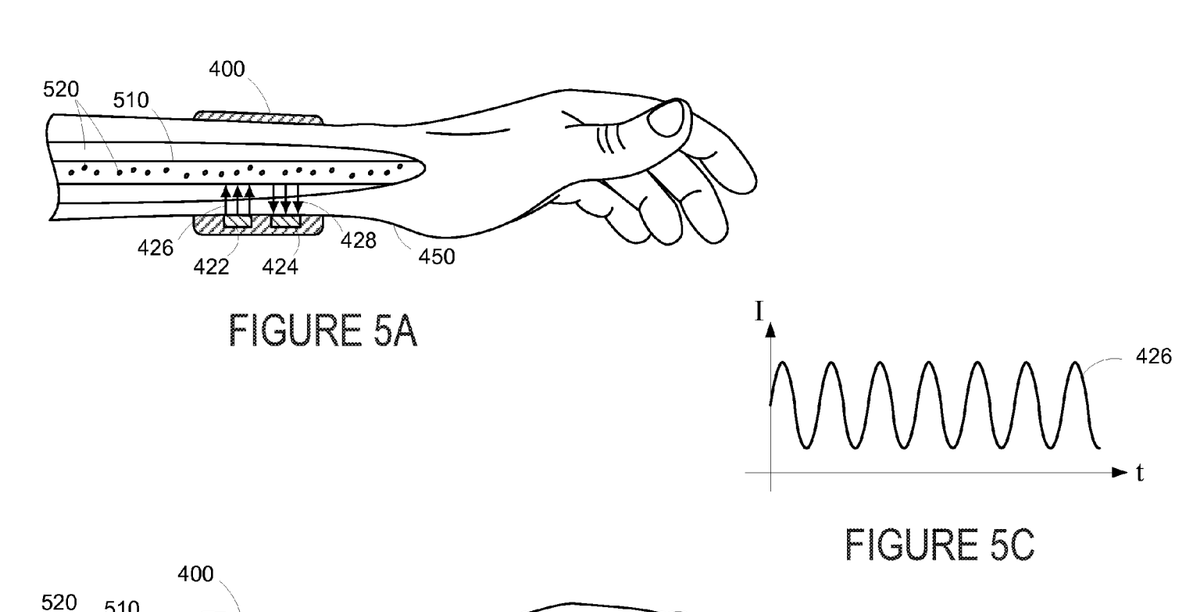
FIG. 5A is a side partial cross-sectional view of a wrist-mounted device, while on a human wrist.
FIG. 5C is a graphical representation of an example modulated reflected light signal.
Figure 5B:
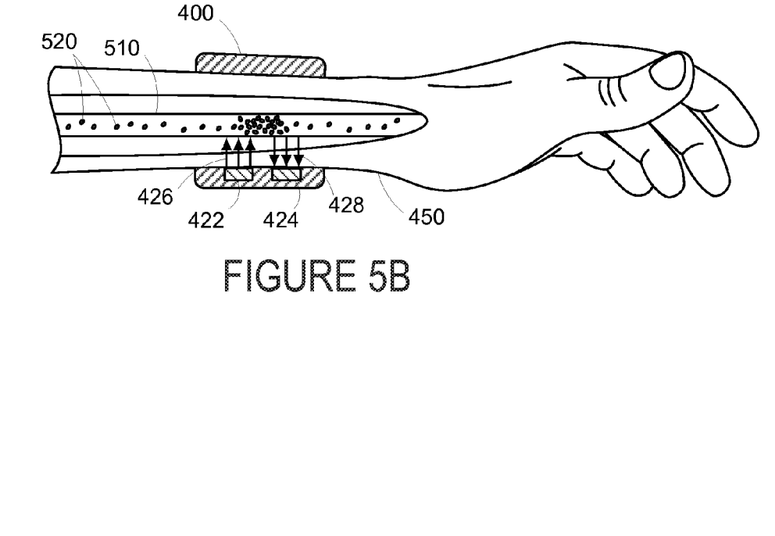
FIG. 5B is a side partial cross-sectional view of a wrist-mounted device, while on a human wrist.

The wearable device 400 may measure pulse rate by sensing the pulsatile increase in blood density resulting from each heartbeat. FIGS. 5A and 5B represent this pulsatile change in blood density that may be detected by the wearable device 400. Light emitted 426 from the light source 422 is directed into a blood vessel of the wearer of the device, is reflected off of one or more objects 520, such as red blood cells, flowing in the blood, and the reflected light 428 is detected by the detector 424. As the wearer's heart beats, waves of denser blood flow past the wearable device 400, as shown in FIG. 5B. The higher density of objects 520 in the blood will cause less light to be reflected back to the detector 424, which will detect a decrease in light intensity. The modulation of the reflected light 428 by the pulsating blood flow may be interpreted by algorithms to produce heart rate, pulse oximetry, and other physiological information. In general, the intensity of light will decrease as the density of blood increases. A graphical representation of this cyclical modulation of the reflected light signal, as detected by the detector 424, is shown in FIG. 5C.

The wearable device 400 may also measure blood oxygen level by sensing differences in reflectance due to the amount of oxygen carried by hemoglobin in the blood. This measurement is based on the principle that oxygenated and unoxygenated hemoglobin have different wavelength sensitive reflectances. In operation, the wearable device 400 directs light of two or more wavelengths into the body. Reflected light is sensed by the detector 424 on the wearable device 400. The difference in reflectance measured at each of the wavelengths over the course of at least one heart cycle may be used to determine a difference in blood oxygen level due to the pulsing blood.

It is also contemplated that the wearable device 400 may be "mounted" to the test model 100 in manners other than that shown in FIG. 3. In some examples, the sensors 420 on the wearable device 400 may be tested prior to attachment of the mount 410, such as a strap. The wearable device 400 may be mounted to the test model 100 with a clamp or other fixation device that does not forma part of the wearable device 400. Alternatively, the test model 100 may be oriented horizontally and the wearable device 400 may be mounted to and held in place on the model layer 120 by gravity or with a weight or clamp. In some cases, the model layer 120 may have a planar portion where the wearable device 400 may be placed.

The test model 100 may be used to simulate at least some of the physiological parameters that may be measured by the wearable device 400 so that the operation and accuracy of the wearable device 400 may be tested and, in some cases, so that the various sensors 420 on the wearable device 400 may be calibrated. For example, to simulate pulse rate, the shaft 112 may be rotated about axis A by a driver or rotary actuator (not shown), which may be provided as part of a control unit 150. As the shaft 112 rotates, the contrast segment 130 will face the test surface 122 and the sensors 420 on the wearable device 400 mounted to the test model 100. Because the contrast segment 130 has a contrasting optical property, e.g. reflectance, from the remainder of the shaft 112, rotation of the shaft 112 will modulate the intensity of the reflected light to simulate the pulsatile blood density indicative of pulse rate. Accordingly, the pulse rate detected by the wearable device 400 will track the rate of rotation of the shaft 130. To simulate blood oxygen saturation, a portion of the rotating shaft may be patterned or treated with or fabricated from materials having different reflectance based on the wavelength of incident light. The characteristics of the contrast segment 130, such as the contrast ratio, shape, symmetry, sharpness or gradient of the contrast change, etc., may be adjusted to simulate or test various different conditions.

Figures 6A, 6B, 6C:
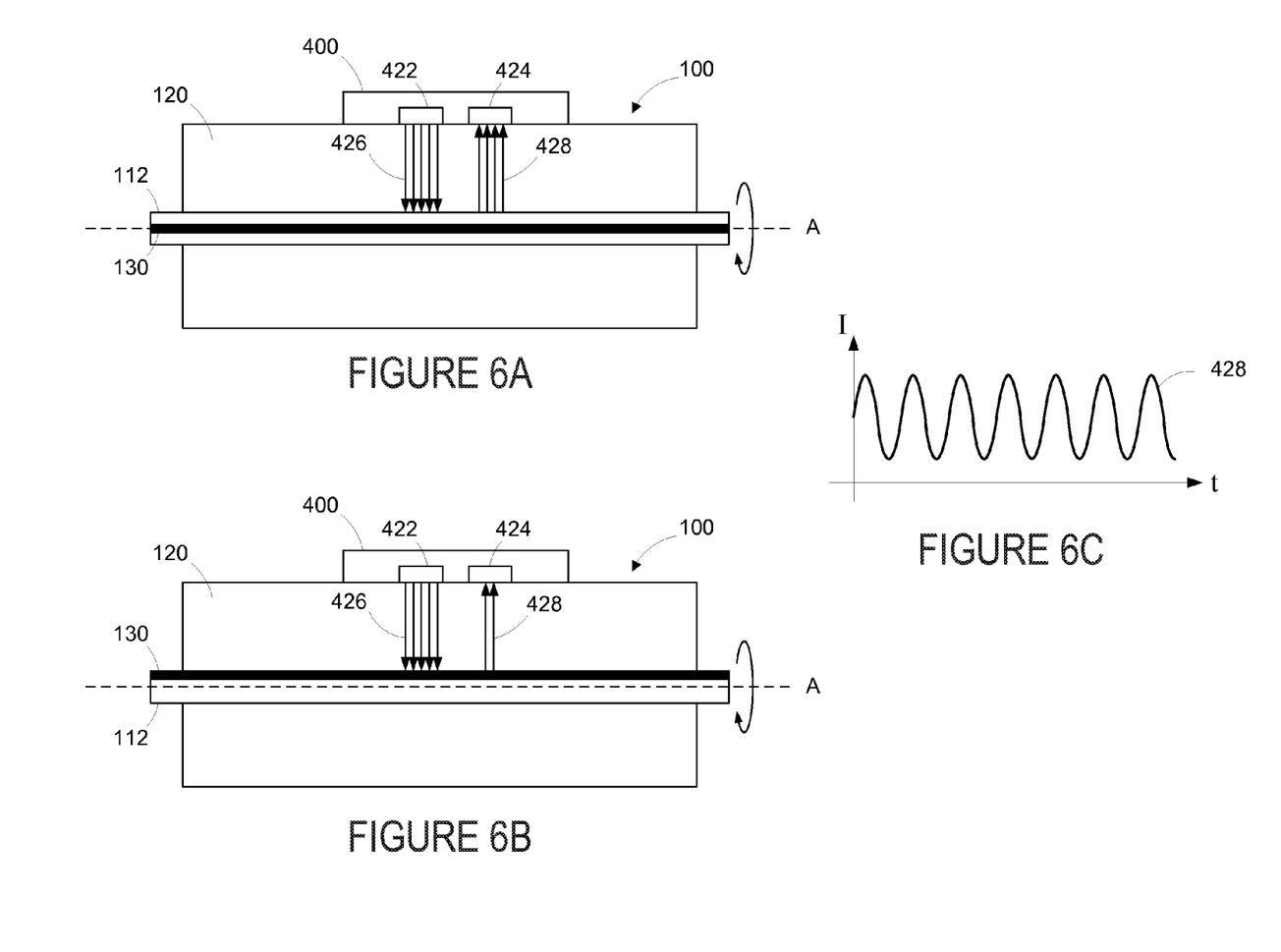
FIG. 6A is a side partial cross-sectional view of a wrist-mounted device, while on a test model.
FIG. 6B is a side partial cross-sectional view of a wrist-mounted device, while on a test model.
FIG. 6C is a graphical representation of an example modulated reflected light signal.

FIGS. 6A-6C illustrate one example of how the test model 100 can simulate one or more physiological parameters, such as pulse rate and blood oxygen level. The shaft 112 is rotated about axis A at a known rate. In some examples, the rate of rotation is chosen to simulate pulse rate, in which each rotation of the shaft 112 translates into one heart cycle. The revolutions per minute of the shaft 112 may correspond to beats-per-minute of a heart rate. Rotation of the shaft 112 causes the contrast segment 130 to face the test surface 122 of the test model 100 and the sensors 422 on the wearable device 400 at various times, based on the rate of rotation. The reflectance of the contrast segment 130 may be lower than the reflectance of the remainder of the shaft 112. The remainder of the shaft 112 may be regarded as a second contrast segment. Accordingly, as shown in FIG. 6B, when the emitted light 426 is incident on the contrast segment 130, less of the emitted light 426 is reflected back to the detector 424. Intensity of the reflected light 428 will be modulated based on rotation of the shaft 112 and contrast segment 130. FIG. 6C is a graphical representation of this cyclical modulation of the reflected light signal, as detected by the detector 424.

The thickness of the model layer 120 or the position of the shaft 112 within the model layer may be varied to control the intensity and diffusion of the reflected light 428 to mimic different physiological characteristics and conditions. Similar to a vein, the shaft 112 may in some examples be placed about 2-3 mm from the test surface 122 of the model layer 120. However, other thicknesses and positions may be used. Typically, the thickness of the model layer 120 (or the depth of the shaft within the layer) will increase diffusion causing the intensity, and changes in intensity, of the reflected light 428 to be less distinct. Similarly, by offsetting the shaft 112 within the model layer 120 such that it is not in the geometrical center and placing a wearable device at different radial positions on the circumference of the model layer (i.e., not directly over the test surface 122, the reflected light intensity may be varied. Controlling the intensity of the reflected light allows the robustness of the sensors 422 on the wearable device and the processing software to be tested.

Rotation of the shaft 112 may be controlled by a control unit 150. Logic executed by a processor (not shown) in the control unit 150 may set the known rate of rotation of the shaft 112 to simulate one or more physiological parameters, such as pulsating blood density. The rate of rotation of the shaft 112 can be adjusted to not only simulate various pulse rates, but also to test the response of a wearable device 300 to pulse rate transients. More specifically, this level of control may be used to determine the amount and effectiveness of a wearable device's filtering algorithms. Abrupt changes in the signal reflected from the body (or test model 100) can make detection difficult, especially due to the high level of noise and the signal-to-noise ratio of the signal. In practice, these abrupt changes may be due to heart rate variability and it is therefore desirable that the wearable device be capable of detecting this variability without losing the reflected signal.

Figure 7:
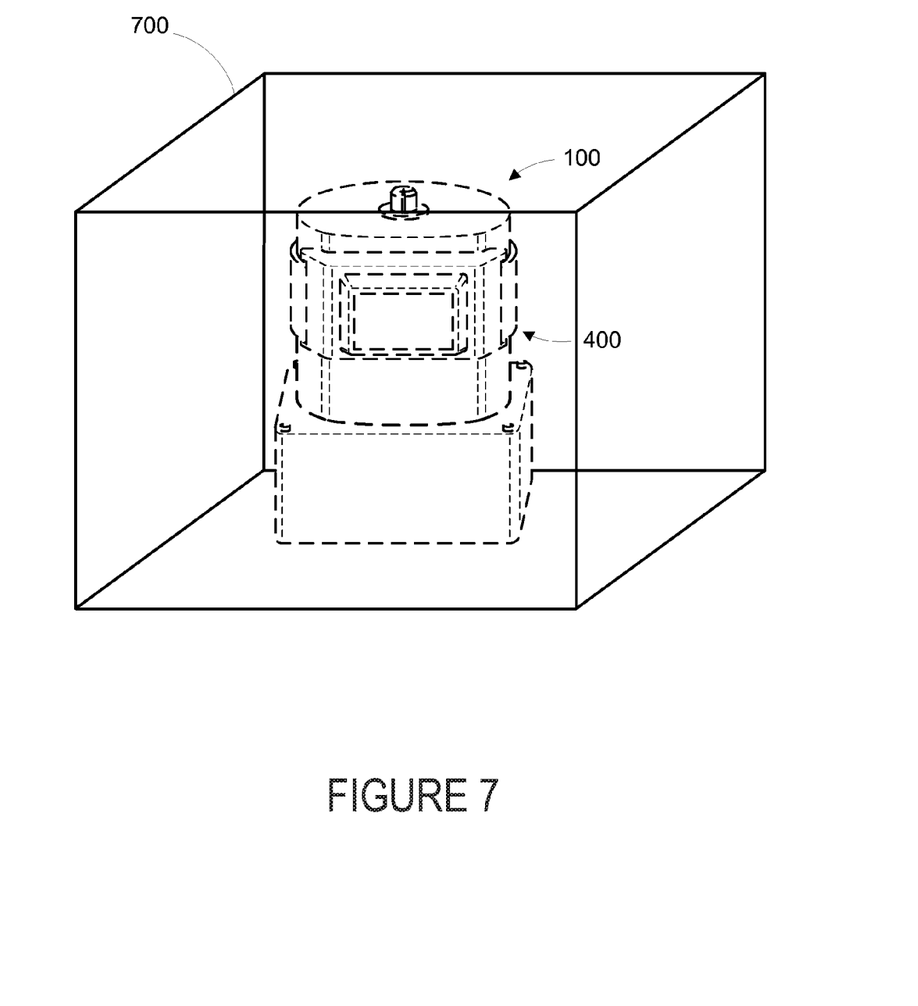
FIG. 7 illustrates a cover over an example test model with an example wearable device mounted thereon.

Features of the wearable device 400 may also be calibrated and/or tested by controlling the amount of ambient light or other external light (light other than what is emitted by the light source 422). The amount of ambient or other external light incident on a portion of the body where the wearable device 400 is worn can affect the signals detected by the device. In one example, ambient light and motion artifacts may be simulated by radiating light, such as from an LED, on or from within the test model. This additional light can shift the intensity of the reflected light 428 detected by the detector 424 on the wearable device 400 under test. Further, movement of the arm (or other body part to which a wearable device is mounted) may cause fluid within the arm to move or tissues to shift. This shifting or movement may cause changes in the intensity of the reflected signal 428. The type of motion artifacts that a wearable device may be subjected to (random, periodic, impulse, etc.) may be simulated by controlling the external light source intensity. In another example, a light blocking cover 700, shown in FIG. 7, may be placed over the entire test model 100 so that light from outside the test environment, such as uncontrolled ambient light variations, do not interfere with the measurements.

Some embodiments of the wearable devices 400 may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a wearer's identity may be treated so that no personally identifiable information can be determined for the wearer, or a wearer's geographic location may be generalized where location information is obtained (such as to a city, ZIP code, or state level), so that a particular location of a wearer cannot be determined.

Additionally or alternatively, wearers of a device may be provided with an opportunity to control whether or how the device collects information about the wearer (e.g., information about a wearer's medical history, social actions or activities, profession, a wearer's preferences, or a wearer's current location), or to control how such information may be used. Thus, the wearer may have control over how information is collected about him or her and used by a clinician or physician or other wearer of the data. For example, a wearer may elect that data, such as health state and physiological parameters, collected from his or her device may only be shared with certain parties or used in certain ways.

III. Example Methods

Figure 8:
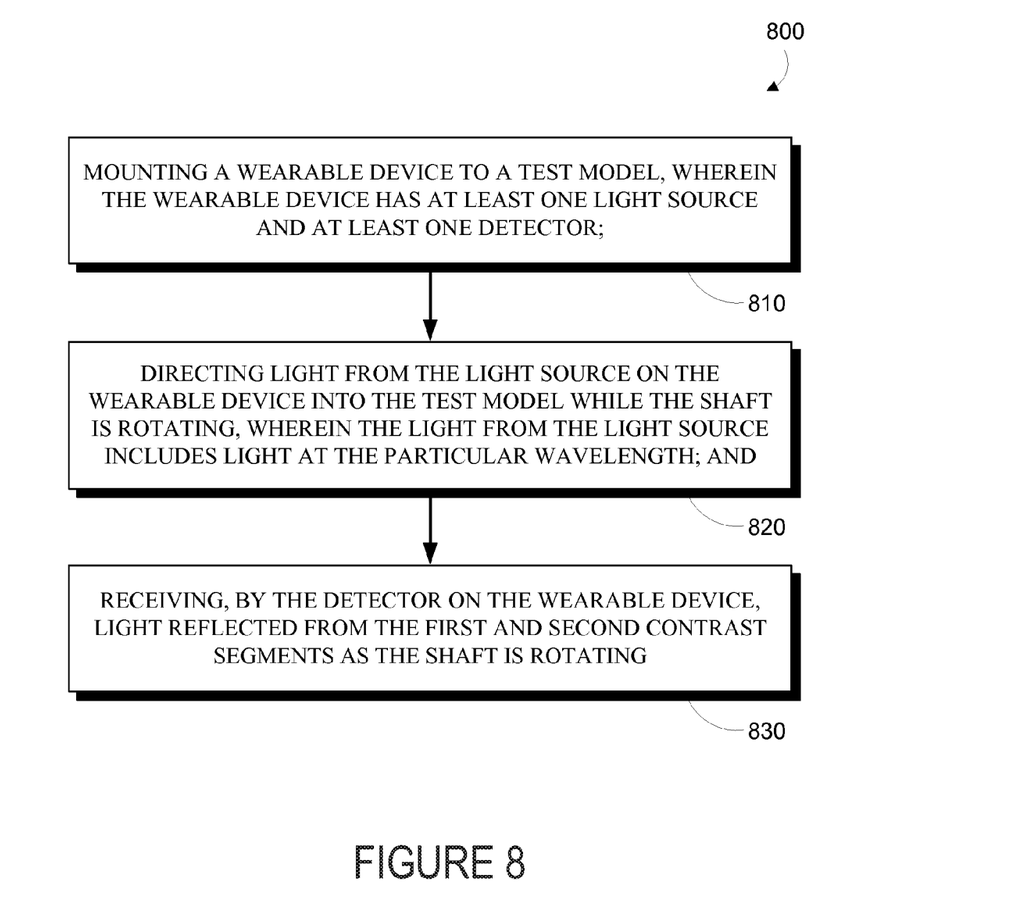
FIG. 8 is a flow chart of an example method, according to an example embodiment.

FIG. 8 is a flowchart of a method 800 for simulating one or more physiological parameters for testing of a wearable device. A wearable device, which may be any of the wearable devices described above having at least one light source and at least one detector, such as wearable device 400, is mounted to a test model (810). The test model, which may include test model 100, comprises a model layer, a shaft rotatably disposed within the model layer, and at least first and second contrast segments circumferentially disposed on the shaft. The model layer models at least one optical property of human skin, such as transmissivity of at least a particular wavelength of light. The first and second contrast segments of the shaft have contrasting optical properties with regard to at least the particular wavelength of light. For example, first contrast segment may correspond to contrast segment 130 and the second contrast segment may correspond to the remainder of the shaft surface. The contrasting optical properties include different reflectances of the particular wavelength of emitted light.

Light at the particular wavelength emitted from the light source on the wearable device is directed into the test model while the shaft is rotating (820) and light reflected from the first and second contrast segments is received by the detector as the shaft is rotating (830). In one embodiment, light reflected from the first contrast segment has a different intensity than the light reflected from the second contrast segment. More particularly, light reflected from the first contrast segment may have a lower intensity than light reflected from the second contrast segment. In a further example, light emitted from the light source may include light at two wavelengths—the particular wavelength and an additional wavelength. The first and second contrast segments may have different reflectances of both the particular wavelength and the additional wavelength. The test model may also be configured to simulate skin temperature and resistance, which may be measured by one or more sensors on the wearable device.

It will be readily understood that the aspects of the present disclosure, as generally described herein, and illustrated in the figures, can be arranged, substituted, combined, separated, and designed in a wide variety of different configurations, all of which are explicitly contemplated herein. While various aspects and embodiments have been disclosed herein, other aspects and embodiments will be apparent to those skilled in the art.

Example methods and systems are described above. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Reference is made herein to the accompanying figures, which form a part thereof. In the figures, similar symbols typically identify similar components, unless context dictates otherwise. Other embodiments may be utilized, and other changes may be made, without departing from the spirit or scope of the subject matter presented herein. The various aspects and embodiments disclosed herein are for purposes of illustration and are not intended to be limiting, with the true scope and spirit being indicated by the following claims.

What is claimed is:

1. A test model, comprising:
    a model layer having a test surface, wherein the model layer models at least one optical property of human skin, wherein the at least one optical property modeled by the model layer includes transmissivity of at least a particular wavelength of light transmitted into the model layer through the test surface;
    an element rotatably disposed within the model layer; and
    at least first and second contrast segments circumferentially disposed on the element such that rotation of the element causes different contrast segments to face the test surface of the model layer at different times, wherein the first and second contrast segments have contrasting optical properties with regard to at least the particular wavelength of light.

2. The test model of claim 1, further comprising two conductive pads disposed on a surface of the model layer and at least one resistor electrically connected between conductive pads.

3. The test model of claim 1, wherein the contrasting optical properties with regard to the particular wavelength of light include different reflectances of the particular wavelength of light.

4. The test model of claim 3, wherein the first contrast segment has a lower reflectance of the particular wavelength of light than the second contrast segment.

5. The test model of claim 3, wherein the first and second contrast segments have different wavelength-dependent reflectances.

6. The test model of claim 5, wherein the at least one optical property modeled by the model layer includes transmissivities of at least the particular wavelength of light and an additional wavelength of light, and wherein the first and second contrast segments have different reflectances of both the particular wavelength and the additional wavelength.

7. The test model of claim 1, further comprising a device for controlling a temperature of at least a portion of the model layer.

8. The test model of claim 7, wherein the device comprises a Peltier device.

9. The test model of claim 1, further comprising a rotary actuator configured to rotate the element within the model layer.

10. The test model of claim 1, wherein the model layer comprises a polymer epoxy and at least one dye.

11. The test model of claim 1, wherein the model layer models a portion of a human arm.

12. The test model of claim 1, wherein the element is a shaft.

13. A method, comprising:
mounting a wearable device to a test model, wherein the wearable device has at least one light source and at least one detector, wherein the test model comprises:
a model layer, wherein the model layer models at least one optical property of human skin, wherein the at least one optical property modeled by the model layer includes transmissivity of at least a particular wavelength of light;
an element rotatably disposed within the model layer; and
at least first and second contrast segments circumferentially disposed on the element, wherein the first and second contrast segments have contrasting optical properties with regard to at least the particular wavelength of light;
directing light from the light source on the wearable device into the test model while the element is rotating, wherein the light from the light source includes light at the particular wavelength; and
receiving, by the detector on the wearable device, light reflected from the first and second contrast segments as the element is rotating.

14. The method of claim 13, wherein the contrasting optical properties with regard to the particular wavelength of light include different reflectances of the particular wavelength of light.

15. The method of claim 14, wherein the light reflected from the first contrast segment has a different intensity than the light reflected from the second contrast segment.

16. The method of claim 14, wherein the light from the light source includes light at the particular wavelength and light at an additional wavelength.

17. The method of claim 16, wherein the first and second contrast segments have different reflectances of both the particular wavelength and the additional wavelength.

18. The method of claim 13, further comprising measuring, by a sensor on the wearable device, a temperature of the test model.

19. The method of claim 13, further comprising measuring, by a sensor on the wearable device, a resistance of the test model.

20. The method of claim 13, wherein the element is a shaft.

* * * * *